(12) United States Patent
Dow et al.

(10) Patent No.: US 8,143,227 B2
(45) Date of Patent: *Mar. 27, 2012

(54) AZITHROMYCIN FOR TREATMENT OF SKIN DISORDERS

(75) Inventors: Gordon Jay Dow, Santa Rosa, CA (US); Bhaskar Chaudhuri, San Jose, CA (US); David Wade Osborne, Fort Collins, CO (US); Barry Calvarese, Menlo Park, CA (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 463 days.

This patent is subject to a terminal disclaimer.

(21) Appl. No.: 12/231,586

(22) Filed: Sep. 4, 2008

(65) Prior Publication Data

US 2009/0062221 A1    Mar. 5, 2009

(51) Int. Cl.
*A61K 31/70* (2006.01)
(52) U.S. Cl. .......................................... 514/29; 536/7.4
(58) Field of Classification Search ............... 514/29
See application file for complete search history.

(56) References Cited

U.S. PATENT DOCUMENTS

| | | | |
|---|---|---|---|
| 5,543,417 A | 8/1996 | Waldstreicher | |
| 6,365,623 B1 * | 4/2002 | Perricone | 514/448 |
| 7,211,267 B2 | 5/2007 | Ashley | |
| 7,704,959 B2 * | 4/2010 | Osborne et al. | 514/29 |
| 2005/0239723 A1 | 10/2005 | Amin | |
| 2006/0280789 A1 | 12/2006 | Ueki | |
| 2007/0105788 A1 | 5/2007 | Mraz-Gernhard | |

OTHER PUBLICATIONS

Amin K, et al, "Common and alternate oral antibiotic therapies for acne vulgaris: a review," Journal of Drugs in Dermatology, 6(9):873-880 (2007).
Basta-Juzbasic A, et al, "A dose-finding study of azithromycin in the treatment of acne vulgaris," Acta Dermatovenerol Croat, 15(3):141-147 (2007).
Beringer, P, et al, "Absolute bioavailability and intracellular pharmacokinetics of azithromycin in . . . ," Antimicrobial Agents and Chemotherapy, 49(12):5013-5017 (2005).
Elewski, BE, "A novel treatment for acne vulgaris and rosacea," European Academy of Dermatology and Venereology, 14:422-430 (2000).
Fernandez-Obregon AF, "Azithromycin for the treatment of acne," International Journal of Dermatology, 39:45-50 (2000).
Gruber F, et al, "Azithromycin compared with minocycline in the treatment of acne comedonica and papulo-pustulosa," Journal of Chemotherapy, 10(6):469-473 (1998).
Kapadia N, et al, "Acne treated successfully with azithromycin," International Journal of Dermatology, 43:766-767 (2004).
Kunynetz, R, "Systemic antibiotic therapy for acne: a review," Skin Therapy Letter, 7(5):3-8 (2002).
Kus S, et al, "Comparison of efficacy of azithromycin vs. doxycycline in the treatment of acne vulgaris," Clinical and Experimental Dermatology, 30:215-220 (2005).
Neu, Hc, "Clinical microbiology of azithromycin," American Journal of Medicine, 91 (suppl 3A):12S-18S (1991).
Riddle, CC, et al, "A review of azithromycin for the treatment of acne vulgaris," Cosmetic Dermatology, 20(5):299-302 (2007).
Pfizer, "Zithromax", (Revised 2007).
Journal of Chinese Physician, 12(4):1411 (2002).

* cited by examiner

*Primary Examiner* — Elli Peselev
(74) *Attorney, Agent, or Firm* — Howard Eisenberg, Esq.

(57) ABSTRACT

Azithromycin has increased efficacy in treating acne and other skin conditions when administered systemically at low doses, below those previously known to produce a clinical antibiotic effect.

23 Claims, 2 Drawing Sheets

AZITHROMYCIN FOR TREATMENT OF SKIN DISORDERS

FIELD OF THE INVENTION

The invention pertains to the field of treatment of dermatologic disorders with systemic pharmacologic therapy. More particularly, the invention pertains to the treatment of skin disorders, such as acne, that are responsive to treatment with systemically administered azithromycin.

BACKGROUND OF THE INVENTION

The skin at times is afflicted with a variety of inflammatory and non-inflammatory disorders. One such disorder is acne, a common disease characterized by various types of lesions. The areas affected typically are areas of the skin where sebaceous glands are largest, most numerous, and most active. The lesions associated with acne are usually categorized as either non-inflammatory or inflammatory. Non-inflammatory lesions include comedones. Comedones appear in two forms, open and closed. Comedones are thought to arise from abnormal follicular differentiation. Instead of undergoing shedding and discharge through the follicular orifice, abnormal desquamated cells (keratinocytes) become unusually cohesive, forming a microcomedone or a microscopic hyperkeratotic plug in the follicular canal. The progression of these microcomedones leads to visible comedones.

For closed comedones, the first sign of inflammation appears along the follicular wall, which then ruptures. Once rupture occurs, the contents of the comedone are extruded into the dermis and cause an increased inflammatory response. Depending on the depth in the dermis and the degree of inflammation, the inflammatory lesion will appear as a pustule, papule, nodule, or cyst. Papules are inflamed, red, tender bumps with no head that range from 2 to 5 mm in diameter. Pustules are papules that are superficial and contain grossly purulent material, that is they have a head with a white or yellow center. Nodules are large, hard bumps 5 mm or more in diameter present under or within the surface of the skin, which can be painful and can last for many months. Cysts are similar to nodules but are pus-filled.

For the purposes of this specification, and unless specified, the term "acne" includes all known types of acne. Types of acne include, for example, acne vulgaris, cystic acne, bromide acne, chlorine acne, comedonal acne, acne conglobata, acne cosmetica, acne estivalis, acne fulminans, halogen acne, iodide acne, acne keloidalis, acne mechanica, nodular acne, non-inflammatory acne, acne papulosa, pomade acne, premenstral acne, acne pustulosa, acne varioliformis, acne venenata, propionic acne, acne excoriee, gram negative acne, steroid acne, inflammatory acne, and nodulocystic acne.

In its mildest form, acne is a more or less superficial disorder characterized by slight, spotty skin irritations involving comedones. In such cases, ordinary skin hygiene, which may include the use of topical keratolytics, typically proves to be a satisfactory treatment. In the more inflammatory types of acne, however, papules; pustules; nodules and cysts; and in extreme cases, canalizing, inflamed and infected sacs, appear. Without effective treatment, these lesions may become extensive and leave permanent, disfiguring scars.

The etiology of acne is multi-factorial. The disease is thought to originate primarily due to increased production of sebum, hypercomification of the infundibulum of pilosebaceous glands, proliferation of microbial flora especially *Propionibacterium acnes*, and subsequent inflammation. *P. acnes* organisms primarily colonize the sebaceous follicles found in the skin, and thus are in a location that is physically sequestered from the skin tissue. Current theories on the pathophysiology of acne hold that the inflammation of acne is due, in part, to an immune reaction to the bacterium or to extracellular products produced in response to the presence of the bacterium, rather than being due to presence of the bacterium itself. Therefore, treatments that are aimed solely at reduction in numbers of *P. acnes* organisms are generally not very effective in long-term treatment of acne. The normal process of epidermal maturation, called keratinization, involves the growing and shedding of cells that line the pores and glands of the skin. In acne, this process is disrupted, causing an overproduction of epithelial cells (hyperkeratosis) in the follicular infundibulum, forming a blockage of the pore.

Mild acne is typically treated with topical cleansers and benzoyl peroxide. Moderate inflammatory acne is often treated with cleansers and keratolytic or comedolytic agents such as retinoids (tretinoin, adapalene or tazarotene), salicylic acid or alpha-hydroxy acids, often in combination with topical or systemic antibiotics. Systemically administered antibiotics, including tetracycline, minocycline, doxycycline, erythromycin, and azithromycin, have been used successfully to treat pustular or papular acne.

Another important skin disorder is rosacea. Rosacea is distinct from acne, although it is sometimes referred to as acne rosacea. Rosacea most commonly affects the skin of the nose and central facial area, and in severe cases involves an extensive area of the face. Forms of acne rosacea include erythematotelangiectatic rosacea, steroid-induced rosacea, papular rosacea, pustular rosacea, ocular rosacea, rhinophymatous rosacea, edematous rosacea, perioral dermatitis, and granulomatous rosacea. Examples of other skin conditions include psoriasis, atopic dermatitis, eczema, irritant contact dermatitis, allergic contact dermatitis, and precancerous skin conditions such as actinic keratosis.

Azithromycin is the generic name for 9-deoxo-9a-aza-9a-methyl-9a-homoerythromycin A, a broad spectrum antibiotic derived from erythromycin A. It was independently discovered by Bright, U.S. Pat. No. 4,474,768 and Kobrehel, U.S. Pat. No. 4,517,359, where it was referred to by the name of N-methyl-11-aza-10-deoxo-10-dihydroerythromycin A. Bright and Kobrehel disclosed azithromycin as a hygroscopic form. Allen, U.S. Pat. No. 6,268,489, discloses a non-hygroscopic dihydrate form of azithromycin. Both the monohydrate form and the dihydrate form are effective in treating bacterial infections when administered systemically in a short course of therapy involving, typically, one to five oral doses.

Several scientific articles have published studies establishing the efficacy of azithromycin in treating inflammatory lesions (papules and pustules) of acne. Femandez-Obregon, International Journal of Dermatology, 39:45-50 (2000), discloses that azithromycin administered in a pulse-dose regimen of 250 mg three times per week is as effective as other antibiotics tested in treating lesions of inflammatory acne. Fernandez-Obregon reported that 19% of the 21 subjects in the study experienced side effects, including 3 cases of gastrointestinal discomfort and one case of vaginitis. Kus et al, Clinical and Experimental Dermatology, 30:215-220 (2005), disclosed that azithromycin dosed at 500 mg for 3 consecutive days per week for 4 weeks, then 2 consecutive days per week for 4 weeks, and then once weekly for 4 weeks was as effective as doxycycline in the treatment of acne. Kus reported that 25 subjects were administered azithromycin in this study. Of these 25, two left the study due to non-compliance and two others left the study due to gastrointestinal side effects.

Similar results have been obtained in other studies of pulse-dosing of azithromycin for the treatment of acne. In Gruber, et al, Journal of Chemotherapy, 10(6):469-473 (1998), azithromycin was pulse-dosed at 500 mg/day for 4 days in four cycles every 10 days. This regimen proved to be efficacious in the treatment of acne and was associated with a gastrointestinal side effect rate of about 10%. Kapadia, International Journal of Dermatology, 43:766-767 (2004), reported successful treatment of acne with 500 mg azithromycin administered three times per week. Adverse events were reported in 11% of subjects. Elewski, European Academy of Dermatology and Venereology, 14:422-430, administered azithromycin at 500 mg on day 1, followed by 250 mg/day for 4 consecutive days beginning on the 1st and 15th day of each month for 3 months. Elewski reported that all patients treated with this azithromycin regimen showed improvement in their acne and only one of twenty subjects experienced gastrointestinal side effects. Elewski further disclosed that intermittent azithromycin offers an effective and rational alternative to systemic antibiotics traditionally used for the management of patients with acne vulgaris or rosacea and could result in a positive impact on patients's quality of life compared with continuous, daily treatment regimens. As stated by Elewski, the pulse dosing regimen for administering azithromycin has been utilized because the long half-life of azithromycin permits the medication to remain in intracellular compartments for prolonged periods at levels higher than the minimum inhibitory concentration for many pathogens.

Recent trends in dosage administration of azithromycin for treatment of skin diseases have been towards higher doses provided in a pulse regimen. Pfizer's Clinical Trial No. NCT00392223 begun in December 2006 and ongoing at the present time tests the efficacy in treating acne with azithromycin in a pulse dosage regimen of 2 grams of azithromycin administered once weekly for 8 weeks.

Tetracyclines are broad spectrum antibiotics that provide their antimicrobial effect by inhibiting protein synthesis by binding to the 30S ribosomal unit. Ashley, U.S. Pat. No. 7,211,267, discloses methods of treating acne by administering a tetracycline compound, such as tetracycline, minocycline, oxytetracycline, and doxycycline. Ashley discloses that tetracycline compounds, which are well known antibiotics, are effective in the treatment of acne even when administered in amounts below that at which the compounds are effective against bacteria. Ashley suggests that treatment with low levels of tetracyclines may cause fewer undesirable side effects than occur with conventional dosages of tetracyclines.

Azithromycin is a member of the macrolide family of antibiotics. In contrast to the tetracyclines, azithromycin and other macrolides such as erythromycin exert their effect by inhibiting RNA-dependent protein synthesis by reversibly binding to the 50S ribosomal unit. Azithromycin has not been shown to be effective in the treatment of acne or other skin disorders at dosages below that which provide the minimum inhibitory concentration in plasma for bacteria associated with acne, such as *P. acnes*.

DESCRIPTION OF THE INVENTION

Figure 1:
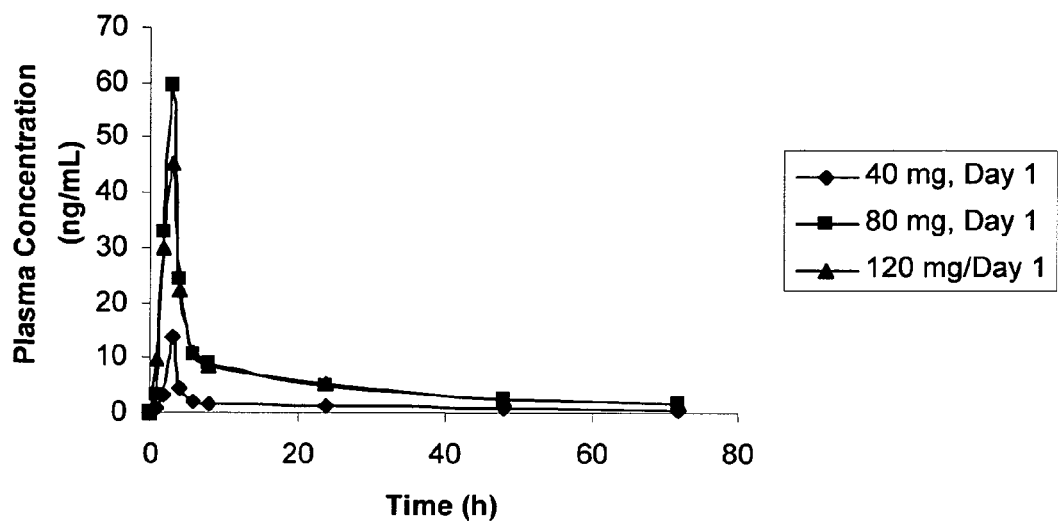
FIG. 1 is a graph showing average plasma concentration (ng/ml) in plasma for 72 hours following an initial dose on day 1 of 40, 80, or 120 mg of azithromycin.

It has been unexpectedly discovered that the systemic administration of azithromycin at dosages well below those previously known to produce a clinical antibiotic effect and believed to be necessary to treat skin disorders, such as acne, atopic dermatitis, or rosacea, is effective in the treatment of such skin disorders. For example, it has been discovered that a dosage of azithromycin below that which provides in plasma the minimum inhibitory concentration (MIC) against *P. acnes* is effective in the treatment of skin disorders such as acne. It has been further unexpectedly discovered that administering azithromycin on a frequent basis, such as daily or every other day, permits the use of very low dosages of azithromycin that are effective in the treatment of skin disorders such as acne. Such low doses have further been discovered to provide an effective steady state level of azithromycin in skin within 20 days or fewer following commencement of therapy, even in the absence of an initial spike dose.

As used herein, the term "daily" means on a daily basis, which includes once per day or multiple times per day.

As used herein, the term "every other day" is synonymous with "alternate day" and encompasses one or more times per day of administration.

Administration of azithromycin at low dosages in accordance with the method of the invention results in improved safety and in the ability to administer the drug regularly for weeks to months, in contrast to the need to intermittently administer azithromycin when it is used for more than just a few days at antibiotic dosage levels, as taught in the prior art. In addition, the incidence of side effects, such as gastrointestinal adverse events including abdominal pain or discomfort, nausea, vomiting and diarrhea, at the low doses in accordance with the present invention is lower than that reported in the prior art.

When administering azithromycin in accordance with the method of the invention, it is preferred to utilize the lowest dose of azithromycin that is effective in reducing the signs and/or symptoms of the skin disorder, such as acne or rosacea, in order to minimize the occurrence of side effects. This is especially preferred with non-acute administration of azithromycin, such as sub-chronic or chronic administration of azithromycin, such as that lasting many weeks, months, or even years.

The low dose administration of azithromycin provides another important advantage. When using an antibiotic dosage level of a drug, the drug kills those bacteria that are most sensitive to the drug, while leaving behind those bacteria that are most resistant. Over time, resistant bacteria outnumber sensitive bacteria and the drug ceases to be useful as an antibiotic due to the predominance of resistant strains.

However, when administering an antibiotic drug at a dosage level below that at which it exerts an antibiotic effect, there is little or no selective pressure on the bacteria exposed to the drug to develop resistance to the drug. Because bacteria that are sensitive to the drug at high dose levels are not killed by the drug at sub-antibiotic levels, the sensitive bacteria do not die and, therefore, selection for antibiotic-resistant bacteria is avoided. Accordingly, the low-dose administration of azithromycin in accordance with the method of the invention minimizes the serious problem of establishing drug-resistant populations of bacteria through the evolutionary selection process.

It has been further unexpectedly discovered that sebum becomes saturated with azithromycin at dosages well below those presently used to treat infectious diseases. The saturated level remains constant even though higher and higher dosages of azithromycin are administered and plasma levels of azithromycin are correspondingly increasing. Thus, dosages of azithromycin that are presently used to treat diseases of the skin, such as those of the pilosebaceous unit, such as acne and papulopustular rosacea, are wasteful and present an unnecessary risk of unwanted side effects, which risk is reduced or even eliminated when using the low dose therapy disclosed herein.

The inventors further theorize that, in addition to the antibiotic effect of azithromycin, there may be a number of other mechanisms that may be responsible for the unexpected effect of low dose azithromycin on acne and other skin disorders. For example, azithromycin may act as a modulator or inhibitor of the activation of Toll-like Receptor-2 or polymorphonuclear leukocytes (PMNs). It is possible that low dose azithromycin, in accordance with the invention, may inhibit the production of pro-inflammatory cytokines, such as IL-1 alpha, TNF-alpha, ICAM-1, or INF-gamma, or may modulate their action. The effectiveness of low dose azithromycin in the treatment of skin disorders, such as acne and rosacea, may be due, at least in part, to a down-regulation or inhibition of human beta defensin 2, the hedgehog signaling pathway, or androgen receptors.

Further, although the inventors wish not to be bound by theory, the attainment of a steady state level of azithromycin provided by low dose daily, or every other day, administration of azithromycin as disclosed herein may result from a more effective "driving in" of the azithromycin to the effective site, such as follicles, pilosebaceous units, sebum, dermis, or epidermis in the case of acne and other skin diseases, than is obtained by administration methods of the prior art, typically by pulse dosing with higher doses. Therefore, lower doses of azithromycin than would be expected to be effective based on the teachings of the prior art have unexpectedly been found to be effective.

As used herein, the term "pulse dosing" refers to a dosage regimen in which, on a weekly basis, the scheduled dose regimen is less frequent than every other day.

One advantage of daily or every other day dosing in accordance with the present invention compared to pulse dosing is increased patient compliance. A single dose on a regular easy-to-remember schedule such as daily or every other day is relatively fool-proof and is conducive to good dosing compliance. Pulse dosing often involves various complicated dosage regimens, such as those described above, which are complex and conducive to patient confusion and non-compliance with the prescribed dosing regimen. Complex and irregular dosing regimens are associated with an increased incidence of missed doses compared to simple and regular dosing regimens. Further, in the case of daily or every other day dosing regimens, the overall therapeutic significance of one or more missed doses is considerably reduced compared with a missed dose in a pulse dosing regimen, The issue of complexity of dosing regimens is especially important with a disease such as acne that predominately affects teenagers. With such individuals, compliance in long term therapy is often a problem. Providing a simple repetitive and easy to remember dosing regimen maximizes the likelihood that an individual, such as a teenager affected with acne, will comply with the regimen. Additionally, pulse dosing as practiced in the prior art, with dosages of 250 mg to 2 grams per day, is accompanied by higher levels of side effects than occurs with daily or pulse dosing with low doses according to the invention.

As used herein, the MIC of azithromycin against *P. acnes*, defined as that concentration that inhibits 90% of growth of the organism, is 150 ng/ml, as reported in Neu, American Journal of Medicine, 91(suppl 3A):3A-12S to 3A-18S (1991). As reported in Neu, the MICs of azithromycin against dermatologically important bacteria other than *P. acnes*, such as *Staphylococcus aureus* which is important in atopic dermatitis, are higher than that for *P. acnes*. The sole exception among dermatologically important bacteria is *Streptococcus pyogenes*, which is important in atopic dermatitis, and which has a reported $MIC_{90}$ of 120 ng/ml, a level that is not significantly different than that for *P. acnes*.

In one embodiment pertaining primarily to acne, but also to skin disorders other than acne, the invention is a method for treating a skin disorder in an individual suffering therefrom comprising systemically administering azithromycin to the individual for a period of time and in an amount that are sufficient to ameliorate the signs and/or symptoms of the skin disorder in the individual, wherein the amount of azithromycin that is administered provides a daily maximum plasma concentration ($C_{max}$) of azithromycin that, when averaged over a period of at least 10 days during which 3 or more azithromycin plasma levels have been determined at 3 following administration of a dose ("average daily $C_{max}$"), preferably based on the mean from a minimum of ten subjects, is less than the MIC for *P. acnes*. Preferably, the $C_{max}$ for each individual day during the period of treatment ("treatment $C_{max}$") is below the MIC for *P. acnes*.

Preferably, the average daily $C_{max}$ does not exceed 0.8 times the MIC for *P. acnes*, and preferably, the treatment $C_{max}$ is not more than 0.8 times the MIC for *P. acnes*. More preferably, the average daily $C_{max}$ does not exceed 0.5 times the MIC for *P. acnes*, and more preferably, the treatment $C_{max}$ is not more than 0.5 times the MIC for *P. acnes*. Even more preferably, the average daily $C_{max}$ does not exceed 0.25 times the MIC for *P. acnes*, and preferably the treatment $C_{max}$ is not more than 0.25 times the MIC for *P. acnes*. And most preferably, the average daily $C_{max}$ does not exceed 0.125 times the MIC for *P. acnes*, and most preferably, the treatment $C_{max}$ is not more than 0.125 times the MIC for *P. acnes*.

Preferably, the azithromycin is administered at least 5 days per week, more preferably at least 6 days per week, and most preferably daily during the period of treatment. If desired, treatment frequency may be every other day. Preferably, the period of treatment is at least 20 days, and conceivably may continue for several months, such as 2 to 3 months, or up to 6 months or more. In cases in which the acne recurs or worsens after the cessation of treatment, it may be preferable to repeat the course of treatment with azithromycin. The low dosages of azithromycin in accordance with invention are safe and effective in treating acne over extended periods of time, in continuous or episodic treatment periods during the acne prone years.

Preferably, the azithromycin is administered on a single administration per day regimen. However, the total daily dosage of azithromycin may be administered in divided dosages to obtain the daily dosage.

Although the preferred administration is daily doses, alternate dosing regimens are also within the scope of the invention provided that the individual dose in a given day is less than 200 mg, and preferably less than 125 mg, and that such alternate dosing regimen is effective for treating the skin disorder. For example, the dose of azithromycin may be administered every other day, daily except for weekends, or several days per week such as on Mondays, Wednesdays and Fridays, or on Tuesdays, Thursdays, Saturdays and Sundays.

The dosage of azithromycin to be administered in accordance with the invention is advantageously less than 125 mg per dose on a given day to an adult human suffering from the signs and/or symptoms of acne or other skin disorder. Thus, the weekly dosage of azithromycin is advantageously 875 mg or less when administered daily and an average of 437.5 mg or less when administered every other day. As used herein, the term "adult" refers to an individual having a body mass of 35 kilograms (77 pounds) or more, such as up to 140 kilograms (310 pounds) or more. For pediatric dosing, less than 35 kilograms, the dosage of azithromycin is typically based on weight. In accordance with the method of the invention, the pediatric dose of azithromycin is less than 5 mg/kg, preferably less than 4 mg/kg, more preferably less than 3 mg/kg, and most preferably less than 2 mg/kg.

Preferably, the dosage of azithromycin that is administered is 120 mg per day or less. More preferably, the dosage is 80 mg per day or less. Most preferably, the dosage is 40 mg per day or less. Examples of daily dosages of azithromycin that are suitable in accordance with the invention include 10, 25, 30, 40, 60, 80, 100, and 120 mg per day, or every other day. When administered every other day, administered doses may be as low as 25 mg per administration and as high as 200 mg per administration. Dosages below 25 mg per day are expected to be efficacious in treating skin diseases. For example, it is conceived that a dosage of as low as 20 mg per day or less may be effective in reducing the signs and/or symptoms of skin diseases responsive to azithromycin, such as acne. It is further conceived that dosages as low as 5 mg per day, or even lower, may provide benefit in treating signs and/or symptoms of skin diseases responsive to azithromycin, including acne.

If desired, a loading dose of greater than 125 mg per day may be administered at the initiation of therapy, such as for the initial dosage or during the first several days or the first week of therapy. As shown below, such a loading dose is not necessary in the treatment of acne and is not preferred due to the increased potential for increased incidence of adverse effects. However, the use of a loading dose, though not preferred, does not take the treatment regimen out of the scope of the present invention, so long as the regimen of the invention is followed thereafter.

Similarly, if desired, an occasional dosage of greater than 125 mg per day, or more than 200 mg if administration is every other day, may be administered during the course of treatment. Such a dosage is not necessary in the treatment of acne. However, the occasional use of such higher dosages does not take the treatment regimen out of the scope of the invention so long as the administration of such higher dosage is occasional, that is it is not administered more than once per week on average during the course of treatment.

The forms of acne that may be effectively treated with this embodiment of the method of the invention, as well as with the other embodiments of the method of the invention, include all known types of acne. Types of acne that may be treated by the methods of the invention include, for example, acne vulgaris, cystic acne, bromide acne, chlorine acne, comedonal acne conglobata, acne cosmetica, acne estivalis, acne fulminans, halogen acne, iodide acne, acne keloidalis, acne mechanica, nodular acne, non-inflammatory acne papulosa, pomade acne, premenstral acne, acne pustulosa, acne varioliformis, acne venenata, propionic acne, acne excoriee, gram negative acne, steroid acne, inflammatory acne, and nodulocystic acne. In a preferred embodiment, the acne that is treated with the method of the invention is acne vulgaris, inflammatory acne, and/or nodulocystic acne. Most unexpectedly, the low doses of azithromycin administered in accordance with the method of the invention are particularly well suited for the effective treatment of the more severe forms and manifestations of acne, such as severe inflammatory acne and nodular acne.

Skin disorders other than acne that are suitable for treatment with this and the following embodiments of the method of the invention include rosacea, including forms of rosacea such as erythematotelangiectatic rosacea, steroid-induced rosacea, papular rosacea, pustular rosacea, ocular rosacea, rhinophymatous rosacea, edematous rosacea, perioral dermatitis, and granulomatous rosacea. Examples of other skin conditions that may be treated in accordance with the method of the invention include psoriasis, impetigo, methicillin resistant *Staph. aureus* (MRSA) skin infections, atopic dermatitis, eczema, irritant contact dermatitis, allergic contact dermatitis, and precancerous skin conditions such as actinic keratosis. The method of the invention is particularly well suited for the treatment of inflammatory skin diseases. The method of the invention is also well suited for treatment of those skin conditions in which sebaceous glands, chemotactic factors, the innate immune system, PMNs, peroxisome proliferator-activated receptors, bacteria, dermal inflammation, or activated Toll-like receptors have a role in the pathogenesis of the condition.

In another embodiment, the invention is a method for treating a skin disorder, such as acne, atopic dermatitis, or rosacea, in an individual suffering signs and/or symptoms therefrom comprising systemically administering azithromycin to the individual for a period of time and in an amount that are sufficient to ameliorate the signs and/or symptoms of the disorder, such as acne or rosacea, in the individual, wherein the amount of azithromycin that is administered provides a level of azithromycin in the skin or in plasma that exhibits minimal variability during the period starting at the attainment of steady state levels of azithromycin, which typically is between 10 and 20 days following the initiation of treatment, until the end of treatment. The maximum variability within an individual during this steady state treatment period is by not more than 50%, preferably by not more than 35%, more preferably by not more than 20%, and most preferably not more than 10% between any two days.

Preferably, the azithromycin is administered on a daily basis, or on a multiple times daily basis, throughout the period of treatment. Preferably, the mean daily dose of azithromycin administered is less than 125 mg. More preferably, the mean daily dose is less than 120 mg. It is even more preferred that the mean daily dose is less than 100 mg. Preferably, the dose that is near the lower end of the lowest effective dose for the particular skin condition being treated should be administered. Preferred mean daily doses may be 120, 110, 100, 90, 80, 70, 60, 50, 40, 30, 20, or 10 mg, or any dose level between 10 and 125 mg. It is conceived that dosages as low as 5 mg, or even lower, may be efficacious in the treatment of acne, or other skin disorder, especially in smaller individuals, such as those less than 50 kilograms.

In accordance with this embodiment of the invention, it is preferred that no daily dose administered after the attainment of steady state levels of azithromycin, typically but not necessarily within 20 days following the initiation of treatment, varies by more than 100% of the dose administered on the previous or following administration of azithromycin. For example, if the daily, or alternate daily, dose is 100 mg, it is preferred that no dose of more than 200 mg be administered on any day of the treatment period. However, the occasional administration, as defined above, of amounts of azithromycin in excess of 100% of the mean daily dose does not take the treatment regimen out of the scope of the invention so long as the administration of such higher dosage is occasional, that is the higher dose of azithromycin is not administered more than once per week on average during the course of treatment.

In another embodiment, the invention is a method for treating a skin disorder, such as acne, atopic dermatitis, or rosacea in an individual suffering signs and/or symptoms therefrom comprising systemically administering azithromycin to the individual for a period of time and in an amount that are sufficient to ameliorate the signs and/or symptoms of the skin disorder, such as acne, atopic dermatitis or rosacea, in the individual, wherein each administration of azithromycin during the treatment period following the attainment of steady state levels of azithromycin, which is typically attained by day 20, is an amount that provides a maximum level of azithromycin in the skin, sebum, and/or follicular casts, following such administration of azithromycin that is no more than 30% higher, preferably no more than 20% higher, and more preferably no more than 10% higher, than the minimum level of azithromycin that was obtained following the previous administration of azithromycin.

According to this embodiment of the invention, the administration of azithromycin is daily, that is, the average period of time between doses is about 24 hours, such as between 12 and 36 hours, or every other day, that is, the average period of time between doses is about 48 hours, such as between 36 and 60 hours. Preferably, each dosage of azithromycin during the once-daily treatment period is administered within 36 hours of the previous dosage, and most preferably, each dosage of azithromycin is administered within 20 to 28 hours of the previous dosage. An occasional missed dose during the course of treatment does not take the treatment regimen out of the scope of the invention.

For maintenance therapy, that is after the signs and/or symptoms of the disorder, such as acne, have responded to the azithromycin therapy of the invention, typically within 2 to 3 weeks following the commencement of therapy, it is preferred that further administration of azithromycin be in accordance with the low-dose azithromycin regimen of the invention. However, if desired, any dosage regimen, such as pulse dosing or the use of higher levels of azithromycin, may also be utilized. Such administration is not preferred because the advantages of the method of the invention, such as increased efficacy, decreased incidence of side effects, particularly gastrointestinal adverse events, and decreased tendency to develop resistance of bacteria to azithromycin, will not be obtained during such maintenance therapy.

Additionally, if desired, the azithromycin dosage regimen of the invention may be preceded by a dosage regimen of azithromycin that is other than that of the present invention. For example, treatment may be initiated with a pulse dosage regimen of azithromycin, followed by a period of dosage in accordance with the invention, which may optionally be followed by a maintenance dosage not in accordance with the invention. Such schemes of administration are not preferred but the period of time that the azithromycin is administered in accordance with the invention is considered to be within the scope of the present invention, so long as such administration is for a period of at least 2 weeks.

It is preferred that the mean dosage of azithromycin calculated on a daily basis is less than 125 mg per day. For example, the daily mean dosage may be any amount between 20 and 120 mg. Doses lower than 20 mg per day are theorized to be effective, for example, in very small individuals, a daily mean dosage of as low as 5 mg or lower may be efficacious. As with the other embodiments of the invention, occasional administrations of azithromycin that do not fall within the method of this embodiment of the invention will not remove the method of administration of azithromycin from the scope of the invention. For example, if a daily dose of azithromycin is missed, a double dose of azithromycin is not required, but optionally may be administered the following day.

In another embodiment of the invention, the invention is a method for treating a skin disorder, such as acne, atopic dermatitis, or rosacea, in an individual suffering signs and/or symptoms therefrom comprising systemically administering azithromycin to the individual for a period of time and in an amount that are sufficient to ameliorate the signs and/or symptoms of the skin disorder, such as acne, atopic dermatitis, or rosacea, in the individual, wherein the azithromycin is administered on a daily basis at a level of less than 125 mg per day or on an alternate day basis in which 200 mg every other day is administered. For example, the daily dosage may be any amount between 5 and 120 mg. As with the other embodiments of the invention, occasional administrations of azithromycin that do not fall within the method of this embodiment of the invention will not remove the method of administration of azithromycin from the scope of the invention.

In all embodiments of methods of the invention, an amount of azithromycin is systemically administered that is less than that previously accepted to be necessary to treat the signs and/or symptoms of skin disorders, such as acne, atopic dermatitis, or rosacea, based on the antibiotic mechanism of action of azithromycin. Preferably, in all embodiments the route of administration is oral. However, any route of administration capable of achieving similar plasma and skin concentrations of azithromycin, such as parenteral, mucosal including sublingual, vaginal, or rectal, and transdermal, is expected by the inventors to have similar efficacy. The orally administered azithromycin may be in any form, including tablets, capsules, powders, powders for suspensions, suspensions, or liquids. It is preferred that the administration of azithromycin in accordance with the embodiments of the invention be on a daily basis, or substantially daily basis—at least 5 times per week, and that the daily administration of azithromycin is at a dosage of less than 125 mg per day. Moreover, it is preferred, but not necessary, that no loading dose of azithromycin be administered at the commencement of therapy. Although not preferred, every other day dosing is within the scope of this invention. With such alternate day therapy, it is preferred that each individual dose does not exceed 200 mg, more preferably does not exceed 150 mg and most preferably does not exceed 125 mg. It is further preferred that the period of therapy be at least 10 days, more preferably at least 14 days, and most preferably at least 20 days.

If desired, the administration of azithromycin in accordance with any of the embodiments of the invention may be provided as part of a co-therapy with one or more other systemic or topical medications effective, either alone or in combination with azithromycin, in the treatment of signs and/or symptoms of a skin disorder, such as acne, atopic dermatitis, or rosacea. For example, a medication, such as a retinoid that is effective against non-inflammatory lesions of skin disorders such as acne may be utilized as a co-therapy with azithromycin. In a preferred embodiment, moderate to severe acne is treated by a co-therapy of azithromycin dosed as described herein and a topical retinoid, such as tretinoin, adapalene, or tazarotene. Such co-therapy may be, for example, by co-administration of the second medication with azithromycin or may be, as another example, by administering the second medication between rounds of azithromycin treatment or before or following treatment with azithromycin.

Examples of topical medications that may be used in combination with azithromycin for the treatment of skin disorders such as acne, atopic dermatitis, and rosacea include corticosteroids, immunosuppressants, anti-infective drugs, anti-inflammatory agents, anti-androgens, adrenergic agonists, immunostimulants, skin barrier repair agents, retinoids, and benzoyl peroxide. Additionally, treatment with other medications, systemic or topical, that are effective in treating or inhibiting the formation of signs and/or symptoms of a skin disorder such as acne, atopic dermatitis or rosacea such as corticosteroids, immunosuppressants, anti-infective drugs, retinoids, and benzoyl peroxide, may be used as maintenance therapy following the cessation of administration of azithromycin.

In another embodiment, the invention is an orally administrable pharmaceutical dosage form or formulation that, when administered to an individual, provides an amount of azithromycin by which the methods of the invention may be achieved. For example, the pharmaceutical dosage form or formulation may be a dosage form or formulation containing azithromycin that, when administered to an individual on a daily basis for a period of two weeks or more, provides a daily maximum plasma concentration ($C_{max}$) of azithromycin that, when averaged over the course of treatment ("average daily $C_{max}$"), is less than the MIC for P. acnes, i.e. 150 ng/ml. Preferably, the $C_{max}$ for each individual day during the period of treatment ("treatment $C_{max}$") is below the MIC for P. acnes.

Alternatively, the pharmaceutical dosage form or formulation of the invention may be a dosage form or formulation containing azithromycin that, when administered to an individual on a daily basis for a period of two months or more, provides an amount of azithromycin that provides a daily maximum level of azithromycin in the skin that does not vary by more than 20%, and preferably not more than 10%, during the period starting at the attainment of steady state levels of azithromycin, which typically is between 10 and 20 days following the initiation of treatment, until the end of treatment.

Alternatively, the pharmaceutical dosage form or formulation of the invention may be a dosage form or formulation containing azithromycin that, when administered to an individual on a daily basis for a period of two weeks or more, provides an amount of azithromycin that provides a maximum level of azithromycin in the skin, sebum, and/or follicular casts, following each administration of azithromycin that is no more than 20% higher, preferably no more than 10% higher, than the minimum level of azithromycin that was obtained following the previous administration of azithromycin.

Alternatively, the pharmaceutical dosage form or formulation of the invention may be a dosage form or formulation that provides an amount of azithromycin of less than 125 mg. For example, the pharmaceutical dosage form or formulation may provide 120, 100, 80, 60, 40, 20, 10, 5, or 1 mg of azithromycin, or any amount between 1 and 120 mg.

It is conceived that the pharmaceutical dosage form or formulation of the invention may comprise azithromycin in an amount that is less than 125 mg, such as 120, 100, 80, 60, 40, 20, 10, 5, or 1 mg of azithromycin, or any amount between 1 and 120 mg. It is noted that orally administrable solid dosage forms, like tablets or capsules, containing an amount of azithromycin less than 250 mg are not available, other than a 100 mg tablet for pediatric patients. It is conceived that the reason for this unavailability of such solid dosage forms is that, prior to the present application, the inventors are unaware of any adult use of azithromycin in dosages less than 250 mg. Accordingly, such dosage forms containing any amount of azithromycin between 1 mg and less than 100 mg, are within the scope of the pharmaceutical dosage form embodiment of the invention, as described more fully below.

Pharmaceutical Formulations Containing Azithromycin

The administration of the pharmaceutical formulation containing the azithromycin may be by any suitable means that results in a concentration of azithromycin that is effective in treating the signs and/or symptoms of skin disorders, such as acne, atopic dermatitis, psoriasis, impetigo, MRSA, eczema, irritant contact dermatitis, allergic contact dermatitis, precancerous conditions such as actinic keratoses, or rosacea. The azithromycin may be contained in the pharmaceutical formulation in any appropriate amount in any suitable carrier substance, and is generally present in an amount of 1-95% by weight of the total weight of the formulation.

The formulation is preferably provided in a dosage form that is suitable for oral administration. Thus, the composition may be in the form of, for example, tablets, capsules, troches, sachets, pills, powders, granules, suspensions, emulsions, solutions, or gels. The pharmaceutical formulations may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Solid Dosage Forms for Oral Use

Formulations for oral use include tablets containing azithromycin in a mixture with pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Examples of other pharmaceutically acceptable excipients include colorants, flavoring agents, plasticizers, humectants, and buffering agents.

The pharmaceutical formulation may contain another drug, in addition to azithromycin. The two drugs of the formulation may be mixed together in the tablet, or may be partitioned. In one example, the first drug is contained on the inside of the tablet, and the second drug is on the outside, such that a substantial portion of the second drug is released prior to the release of the first drug. Drugs that may be combined with azithromycin for the treatment of a skin condition include but are not limited to corticosteroids, immunosuppressants, anti-infective drugs, vitamin A, retinoids such as 13-cis retinoic acid, anti-inflammatory agents, adrenergic agonists, and anti-androgens.

As known in the art, tablet blends may be dry-granulated or wet granulated before tableting. Alternatively, tablet blends may be directly compressed. The choice of processing approach depends upon the properties of the drug and chosen excipients, for example particle size, blending compatibility, density and flowability. For azithromycin tablets, granulation is preferred, with wet granulation being most preferred. Azithromycin may be wet-granulated, and then other excipients may be added extragranularly. Alternatively, azithromycin and one or more excipients may be wet-granulated. In addition, tablets may also be coated, with a coating that exhibits little or no effect on or interference with tablet dissolution, to assure ease of swallowing or to provide an elegant appearance, or to protect the composition from unwanted chemical changes, (e.g., chemical degradation prior to the release of the active drug substance). The coating may be applied on the solid dosage form in a similar manner as that described in Encyclopedia of Pharmaceutical Technology, supra.

If desired, tablets containing azithromycin may be film-coated to provide ease of swallowing and an elegant appearance. Many polymeric film-coating materials are known in the art. A preferred film-coating material is hydroxypropylmethylcellulose (HPMC). HPMC may be obtained commercially, for example from Colorcon Corp., in coating formulations containing excipients which serve as coating aids, under the registered trademark Opadry. Opadry formulations may contain lactose, polydextrose, triacetin, polyethyleneglycol, polysorbate 80, titanium dioxide, and one or more dyes or lakes. Other suitable film-forming polymers also may be used herein, including, hydroxypropylcellulose, and acrylate-methacrylate copolymers.

The tableting process itself may otherwise employ conventional procedures and equipment known to those skilled in the art and may readily be practiced by forming a tablet from a desired blend or mixture of ingredients into the appropriate shape using a conventional tablet press. Tablet formulation and conventional processing techniques have been widely described, for Example in Pharmaceutical Dosage Forms: Tablets; Edited By Lieberman, Lachman, and Schwartz; Published by Marcel Dekker, Inc., 2d Edition, Copyright 1989, the text of which is herein incorporated by reference.

In addition to tablets that are administered by swallowing whole, other examples of solid formulations for oral use include chewable tablets, hard gelatin capsules wherein the active ingredient is mixed with an inert solid diluent (e.g., potato starch, lactose, microcrystalline cellulose, calcium carbonate, calcium phosphate or kaolin), and soft gelatin capsules wherein the active ingredient is mixed with water or an oil medium, for example, peanut oil, liquid paraffin, or olive oil. Powders and granulates may be prepared using the ingredients mentioned above under tablets and capsules containing such powders or granules may be made in a conventional manner using, e.g., a mixer, a fluid bed apparatus or a spray drying equipment.

Liquids for Oral Administration

Powders, dispersible powders, or granules suitable for preparation of an aqueous suspension by addition of water are convenient dosage forms for oral administration. Formulation as a suspension provides the azithromycin in a mixture with a dispersing or wetting agent, suspending agent, and one or more preservatives. Suitable dispersing or wetting agents are, for example, naturally-occurring phosphatides (e.g., lecithin) or condensation products of ethylene oxide with a fatty acid, a long chain aliphatic alcohol, or a partial ester derived from fatty acids, and a hexitol or a hexitol anhydride (e.g., polyoxyethylene stearate, polyoxyethylene sorbitol monooleate, polyoxyethylene sorbitan monooleate, and the like). Suitable suspending agents include, for example, sodium carboxymethylcellulose, methylcellulose, and sodium alginate.

In the preparation of azithromycin powder for oral suspension formulations, all ingredients may be blended together and deagglomerated, as known in the art. Preferably, azithromycin and flavors are blended, and other ingredients are separately blended. Finally, these two blends are blended and deagglomerated.

Preferred oral suspensions are those which resuspend easily after constitution with aqueous media and which do not cake on storage after constitution. Preferred suspensions contain sucrose NF, when sucrose is used, and anhydrous excipients when available, to assure facile suspension upon constitution. The drug-containing powder is generally reconstituted with water.

An azithromycin unit dose packet dosage form (also referred to herein as a "sachet") consists of a unit packet, designed to be emptied into an aqueous vehicle, for example water or a natural or artificial fruit beverage. The packet contains a blend of azithromycin and excipients which is thus reconstituted. The packet contains, as necessary ingredients, azithromycin and a dispersing agent which makes the sachet powder free flowing, for example colloidal silicon dioxide such as Cab-O-Sil from Cabot. Generally the dispersing agent is present in an amount of about 0.2 to 2.0% by weight based on the weight of the dry sachet as it is to be sold. The dispersing agent also serves as a glidant. The formulation may also optionally contain ingredients including (1) a filler or sweetener (e.g. glucose); (2) a buffer (e.g. sodium phosphate); (3) a wetting agent such as a surfactant, for example sodium lauryl sulfate, and (4) flavors such as any of those enumerated herein. The powder in the packet flows freely and disperses quickly, essentially immediately upon stirring when reconstituted. Azithromycin unit dose packet dosage forms may be prepared by blending and deagglomerating all ingredients, as known in the art. Preferably, the filler (e.g. sucrose), buffer (e.g. anhydrous tribasic sodium phosphate), and glidant (e.g. colloidal silicon dioxide) are blended and deagglomerated, followed by blending with azithromycin and flavors, followed by deagglomeration.

Any excipients used in making the oral dosage form of the invention, whether in solid or liquid form, whether as a tablet, capsule, or other form, should be pharmaceutically acceptable and compatible with the azithromycin in the dosage form. The azithromycin in the dosage form may be in one or more of several forms, including azithromycin dihydrate and azithromycin monohydrate. In addition, it is preferred that the oral dosage form should be physically and chemically stable for a commercially reasonable period of time, for example when stored at room temperature for 18 months.

The oral dosage forms of this invention may be packaged in multiple dose containers such as jars or bottles in an amount sufficient for a suitable period of time such as 2 weeks, one month, or for a prescribed course of therapy. In one preferred embodiment of the invention, a kit is provided which contains a multiplicity of azithromycin oral dosage forms, such as tablets or capsules, a primary packaging such as a jar containing the oral dosage forms, and instructions for use to administer the oral dosage forms in accordance with the method of the invention. Unit dose packaging such as sachets or blister packs provide a useful way of packaging the oral dosage form of this invention, and may embody a kit when combined with instructions for use. Detailed product information may be included with the instructions for use in kit embodiments of the invention. Blister packaging is particularly useful with solid oral dosage forms and is preferred for alternate day dosing schedules for example. In one preferred embodiment, solid unit dosage forms of azithromycin of 125 mg or less are included in a blister pack with instructions to administer one or more tablets or capsules on a daily basis so that the dosage of azithromycin is 125 mg or less per day. In another preferred embodiment, solid unit dosage forms of azithromycin of 200 mg or less are included in a blister pack with instructions to administer one or more tablets or capsules on an alternate day basis so that the dosage of azithromycin is 200 mg or less per day of administration.

The invention is further illustrated by the following non-limiting examples.

EXAMPLE 1

Azithromycin Levels in Plasma

Plasma levels of azithromycin were determined as follows. Thirty-nine patients were randomized into one of three treatment groups. Each patient received 40 mg (n=13), 80 mg (n=11), or 120 mg (n=15) of oral azithromycin daily. After the initial dose on day 0, a second dose was not administered until 72 hours later, so as to permit measurement of plasma levels based on a single dose and determination of pharmacokinetic parameters. Blood samples from each patient were taken at times equal to 0 (before dosing), 1, 2, 3, 4, 6, 8, 24, 48, and 72 hours after the initial oral dose. Following 72 hours, each patient received azithromycin daily for the remainder of six weeks (42 days). Blood samples were also taken at times equal to 0 hours (before dosing) and 3 hours after dosing on day 21, and at times equal to 0, 1, 2, 3, 4, 6, 8, and 24 hours following the last dose given on day 42. Plasma samples obtained from the blood samples were stored at −20° C. or lower after collection until processing and analysis.

The amount of azithromycin in plasma was quantified using a validated high pressure liquid chromatographic assay with mass spectroscopy detection. Standards and samples were treated, by pipet addition, with 10.0 microliter of 1:1 acetonitrile/water. The standards and samples were then treated, by pipet addition, with 10.0 microliter of an Aza-erythromycin A internal standard solution, followed by the addition of 2.0 mL of the mobile phase, which contained a 250:150:100:0.5:0.1 mixture of ethyl acetate, methanol, acetonitrile, formic acid and morpholine. After tightening Teflon caps onto the extraction jars containing the treated standards and samples, the jars were rotated for 2 hours at 1 rps. Next, 0.20 mL aliquots were removed from each jar and transferred to HPLC autosampler vials, and the vials capped and placed in the autosampler tray for LC-MS-MS analysis. A 5 microliter aliquot was injected from each vial into a suitable high pressure liquid chromatograph (HPLC) with suitable mass spectrophotometry-mass spectrometery detection, such as a Sciex API 3000 LC-MS-MS (GenTech Scientific, Inc., Arcade, N.Y.) with heated nebulizer source. The column used was PVA-Sil, 5 micron, 4.0×50 mm cartridge (Waters Corporation, Milford, Mass.). The flow rate was 1 ml/minute. To determine the amount of azithromycin, the peak area of the m/z 750→592 azithromycin product ion was measured against the peak area of the m/z 736→578 azaerythromycin A internal standard product ion.

Following the administration of a single dose of azithromycin, $C_{max}$ was attained within 3 hours at all dosages tested. The obtained $C_{max}$ was less than the MIC against $P.$ $acnes$ at each measurement. Data for average azithromycin plasma concentration (ng/ml) among subjects for 72 hours following the initial dose for each of the three treatment groups is shown in FIG. 1 and data for average azithromycin plasma concentration among subjects following administration on day 42 (last dose) for each of the three treatment groups is shown in FIG. 2.

As shown in FIG. 1, the average plasma level of azithromycin among subjects peaked for each treatment group at 3 hours post administration and then rapidly decreased until 5 hours. From that time until the end of the test at 72 hours, average azithromycin plasma levels decreased gradually to less than 2 ng/ml for each group. FIG. 1 further shows that for each dose the average peak plasma concentration never reached the MIC of 150 ng/ml for azithromycin against $P.$ $acnes$. The average maximum azithromycin plasma level among subjects for the 40 mg/day, 80 mg/day, and 120 mg/day treatment groups was, respectively, about 15 ng/ml, 59 ng/ml, and 45 ng/ml.

Figure 2:
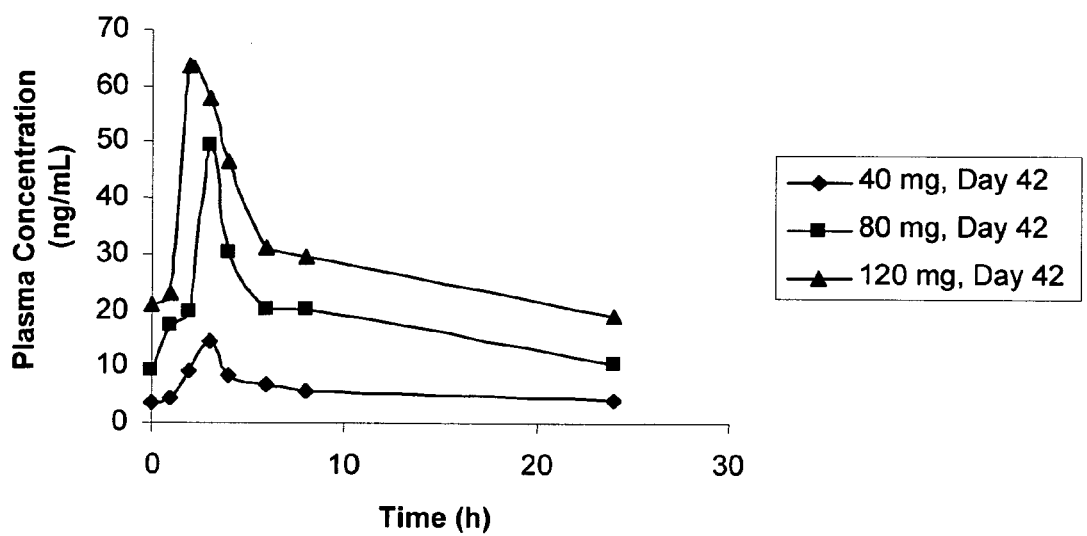
FIG. 2 is a graph showing average plasma concentration (ng/ml) in plasma for 24 hours following a daily dose of 40, 80, or 120 mg of azithromycin administered on the 42nd consecutive day of treatment.

As shown in FIG. 2, average azithromycin plasma levels following the attainment of steady state conditions were about 4 ng/ml, 10 ng/ml, and 22 ng/ml, respectively for the 40 mg/day, 80 mg/day, and 120 mg/day treatment groups. Following administration of azithromycin on day 42, the average maximum azithromycin plasma level among subjects for the 40 mg/day, 80 mg/day, and 120 mg/day treatment groups was, respectively, about 16 ng/ml, 54 ng/ml, and 68 ng/ml, well below the MIC for azithromycin against $P.$ $acnes$ of 150 ng/ml. The median plasma $C_{max}$ at day 42 were also well below the MIC for azithromycin against $P.$ $acnes$ as were the MICs for azithromycin against $Staphylococcus$ $aureus$ and $S.$ $pyogenes$.

Plasma azithromycin concentrations were tabulated for each of the subjects for each dose group 40 mg/day, 80 mg/day, and 120 mg/day, respectively. The pharmacokinetic evaluation was based on individual plasma concentration-time data of azithromycin and was performed using model-independent analysis methods within WinNonlin™ version 5.0.1 (Pharsight Corporation, Mountain View, Calif.). Table 1 shows the median values for the following pharmacokinetic parameters, $C_{max}$, $AUC_{last}$, and $AUC_{24}$. $C_{max}$, the maximum plasma concentration, was obtained directly from the concentration-time data. $AUC_{last}$, the area under the plasma concentration-time curve from time 0 to time t (the time of last quantifiable plasma concentration), was calculated using the linear trapezoidal rule from predose to the last quantifiable plasma concentration. $AUC_{24}$, the area under the plasma concentration-time curve from time 0 to time t=24 hours, was calculated in a manner similar to the calculation for $AUC_{last}$ except from predose to 24 hours.

TABLE 1

Pharmacokinetic Parameters (median) - Azithromycin

| | DOSAGE | | |
|---|---|---|---|
| | 40 mg/day | 80 mg/day | 120 mg/day |
| Cmax (ng/ml) | | | |
| Day 0 | 7.08 | 60.30 | 57.90 |
| Day 42 | 13.75 | 53.85 | 92.90 |
| $AUC_{last}$ (ng * h/ml) | | | |
| Day 0 | 73.43 | 456.47 | 433.15 |
| $AUC_{24}$ (ng * h/ml) | | | |
| Day 0 | 44.67 | 294.38 | 292.87 |
| Day 42 | 132.27 | 528.48 | 751.98 |

As shown in Table 1, the maximum plasma concentration on day 0 and on day 42 for all dosages tested was less than the MIC of azithromycin for $P.$ $acnes$. As shown in Table 1, the initial single dose pharmacokinetic data did not show difference in pharmacokinetic parameters between 80 mg/day and 120 mg/day. Upon reaching steady state, azithromycin dose is proportional to $AUC_{(24)}$ and to $C_{max}$ for the 80 mg/day and 120 mg/day dosages. Relative to dose, the AUC values for the 40 mg/day azithromycin dose were not proportional to the higher dose levels of 80 mg/day and 120 mg/day.

EXAMPLE 2

Azithromycin Levels in Sebum

Sebum was collected from the subjects of Example 1 by use of Sebutape® (CuDerm Corporation, Dallas Tex.). On study days 0, 21, 42, and 70, each subject placed three Sebutape® adhesive patches on each of the forehead, and left and right cheeks on the skin of the face and left the patches in place for 30 to 40 minutes. The patches were then removed, folded in half with the adhesive side inward, placed in a sealed glass vial, and frozen at −20° C. to −70° C.

The sebum collected in each Sebutape® adhesive patch was extracted and quantified utilizing the procedure of Example 1 pertaining to azithromycin in skin. Each Sebutape® patch was analyzed for quantity in nanograms of azithromycin. This quantity was divided by 1.38 mg (the average weight of sebum that was determined to be in each adhesive patch) to obtain a concentration of azithromycin (ng azithromycin/mg sebum) in the sample. This value was converted to a concentration (ng azithromycin/microliter sebum) by multiplying this value by 0.87 mg/µl, the density of sebum. The results are shown in Table 2 and in FIG. 3.

TABLE 2

Sebum Concentration (median) - Azithromycin

| | DOSAGE | | | | | | | | |
|---|---|---|---|---|---|---|---|---|---|
| | 40 mg/day | | | 80 mg/day | | | 120 mg/day | | |
| | ng per sample | ng/mg[1] | ng/µl[2] | ng per sample | ng/mg[1] | ng/µl[2] | ng per sample | ng/mg[1] | ng/µl[2] |
| Day 0 | 0.00 | .00 | .00 | 0.00 | .00 | .00 | 0.00 | .00 | .00 |
| Day 21 | 0.00 | .00 | .00 | 0.79 | .57 | .50 | 0.76 | .55 | .48 |
| Day 42 | 0.19 | .14 | .12 | 0.84 | .61 | .53 | 0.88 | .64 | .55 |
| Day 70 | 0.00 | .00 | .00 | 0.00 | .00 | .00 | 0.00 | .00 | .00 |

[1] = ng per sample divided by 1.38 mg, the average quantity of sebum in each sample

[2] = ng azithromycin per mg sebum times 0.87 mg/µl, the density of sebum

Figure 3:
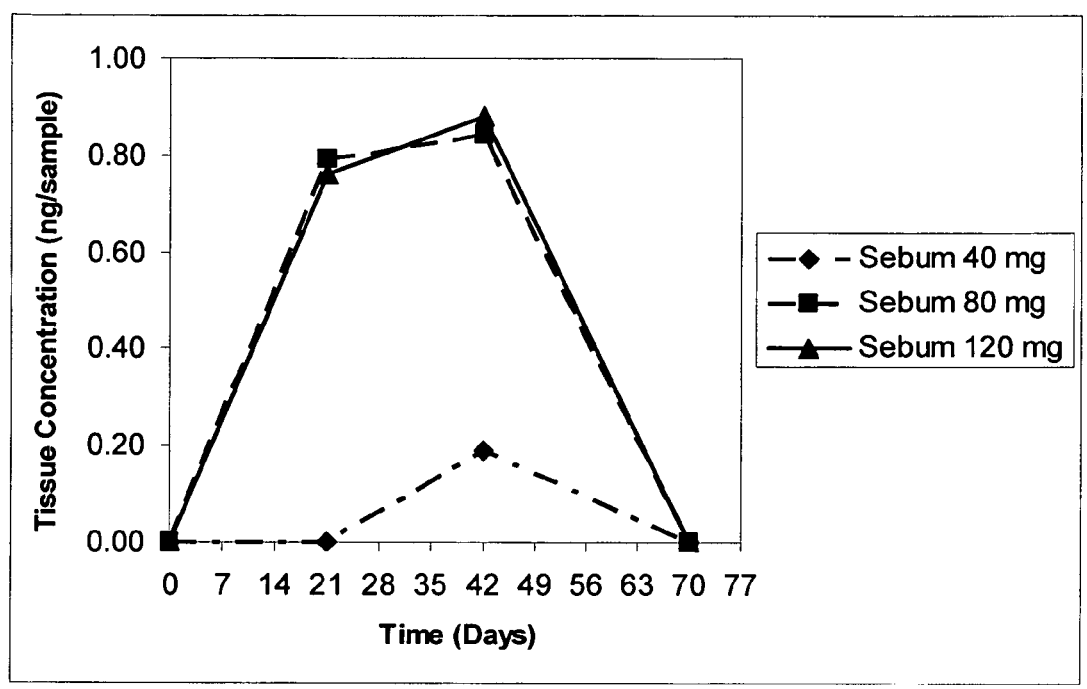
FIG. 3 is a graph showing the concentration in sebum of azithromycin over time when administered at a dosage of 40, 80, or 120 mg per day for 42 days.

As shown in Table 2 and FIG. 3, the amount of azithromycin in each Sebutape® sample increased with increasing dose until a maximum amount of about 0.88 ng of azithromycin was obtained in 1.38 mg of sebum, equivalent to about 0.64 ng of azithromycin per mg of sebum or about 0.55 ng of azithromycin per microliter of sebum. The azithromycin in the samples was about the same for the dosages of 80 mg per day and 120 mg per day. The data indicates that the saturation concentration of azithromycin in sebum is obtained between the dosages of 40 and 80 mg per day.

Sebum levels of azithromycin at day zero were the same for each group. The data of Table 2 indicates that doses of azithromycin according to the invention are needed for many days, such as 20 or 21 days, to achieve measurable or saturated concentrations of azithromycin in sebum of human subjects. It is theorized that the unexpected efficacy of the low dose azithromycin method of the invention is due in part to the systematic and stepwise loading of azithromycin in sebum to significant measurable or saturated levels. It is further theorized that, once significant measurable or saturated levels of azithromycin are attained and therapy is terminated, clearance of azithromycin from the sebum occurs over a prolonged period, which further contributes to the expected efficacy observed with the method of the invention.

It is theorized that daily doses of azithromycin more than three times the dose needed for achieving saturated sebum levels (sebum saturating dose) are not necessary for the successful treatment of skin diseases such as acne, rosacea or atopic dermatitis. It is further theorized that it is preferable to administer not more than two times the sebum saturating dose, and more preferable to administer not more than one and one-half the sebum saturating dose.

EXAMPLE 3

Azithromycin Levels in Skin

Standardized follicular biopsy samples, representative of the pilosebaceous unit of the skin, were obtained from the upper back from each of the subjects of Example 1 on study days 0, 21, 42, and 70. The samples were analyzed to determine the tissue level of azithromycin in each biopsy sample. The results are shown in Table 3.

TABLE 3

Skin Concentration (median) - Azithromycin - ng/sample

| | DOSAGE | | |
|---|---|---|---|
| | 40 mg/day | 80 mg/day | 120 mg/day |
| Day 0 | 0.00 | 0.00 | 0.00 |
| Day 21 | 0.34 | 1.34 | 1.65 |
| Day 42 | 0.59 | 1.68 | 1.99 |
| Day 70 | 0.00 | 0.47 | 0.50 |

As shown in Table 3, the median amount of azithromycin in the skin follicular biopsy samples increased with increasing dosage of azithromycin. The difference in amount of azithromycin obtained between the 80 mg/day and 120 mg/day dosages is significantly less than the difference obtained between the 40 mg/day and 80 mg/day dosages. This data indicates that the skin, and particularly the pilosebaceous unit as shown by the follicular biopsy, becomes saturated with azithromycin at a dosage between 80 and 120 mg per day. It is theorized from this data that the skin becomes saturated with azithromycin at a dosage of about 95 mg/day. It is further unexpectedly observed with the low dose azithromycin regimen of this invention that the clearance of azithromycin from the pilosebaceous apparatus, which contains epithelial cells as well as sebum, is significantly slower (more than 28 days) after attaining saturation or near saturation levels of azithromycin in the tissue.

EXAMPLE 4

Gastrointestinal Side Effects

The subjects of Example 1 were monitored for the presence of gastrointestinal adverse effects during the six weeks (42 days) of treatment with the daily low-dose azithromycin of the invention and for an additional 4 weeks (total of 70 days) following cessation of treatment. During this time, no gastrointestinal side effects were reported by any of the subjects receiving any of the dose levels, 40, 80, or 120 mg/day.

EXAMPLE 5

Efficacy Against Acne

The subjects of Example 1 were evaluated for efficacy of each dosage (40 mg, 80 mg, or 120 mg per day) in treating moderate to severe acne following treatment for 6 weeks. Before starting the treatment protocol, the number of facial non-inflammatory lesions (open and closed comedones), inflammatory lesions (papules, pustules, and nodules), and nodules were counted. The numbers of these lesions were counted again at day 21 of treatment and at day 42. The % decrease from Day 0 was calculated as the mean of the differences for each of the parameters (non-inflammatory lesions, inflammatory lesion and nodules) for each individual subject on Day 21 and Day 42. The results, including average lesion counts and efficacy assessment by percent decrease in lesion counts, are shown for the 40 mg, 80 mg, and 120 mg group, respectively, in Tables 4, 5, and 6.

TABLE 4

Azithromycin 40 mg/day for 6 weeks

| | Day 0 | Day 21 | % Decrease from Day 0 | Day 42 | % Decrease from Day 0 |
|---|---|---|---|---|---|
| Inflammatory lesions | 30.1 | 14.4 | 51.5% | 13.8 | 54.2% |
| Non-inflammatory lesions | 36.5 | 23.9 | 30.4% | 21.5 | 38.9% |
| Nodules | 5.2 | 2.2 | 62.4% | 1.2 | 82.2% |

TABLE 5

Azithromycin 80 mg/day for 6 weeks

| | Day 0 | Day 21 | % Decrease from Day 0 | Day 42 | % Decrease from Day 0 |
|---|---|---|---|---|---|
| Inflammatory lesions | 37.0 | 19.8 | 44.7% | 17.0 | 53.7% |
| Non-inflammatory lesions | 38.7 | 24.9 | 34.7% | 29.3 | 24.7% |
| Nodules | 5.5 | 1.5 | 72.8% | 1.3 | 74.2% |

TABLE 6

Azithromycin 120 mg/day for 6 weeks

| | Day 0 | Day 21 | % Decrease from Day 0 | Day 42 | % Decrease from Day 0 |
|---|---|---|---|---|---|
| Inflammatory lesions | 31.6 | 15.6 | 51.9% | 14.8 | 52.9% |
| Non-inflammatory lesions | 37.7 | 27.8 | 28.1% | 23.2 | 38.9% |
| Nodules | 4.7 | 1.0 | 78.6% | 1.1 | 73.7% |

As shown in Tables 4 to 6, following treatment with any of 40, 80, or 120 mg of azithromycin per day, there was a marked decrease in the number of inflammatory acne lesions at 21 days and at 42 days of treatment. Tables 4 to 6 also show that non-inflammatory acne lesions responded favorably to daily treatment with azithromycin at each dosage level tested, 40, 80, or 120 mg. Tables 4 to 6 further show that, following treatment with any of 40, 80, or 120 mg of azithromycin, there was a marked decrease in the number of facial nodules at both 21 and 42 days of treatment.

EXAMPLE 6

Additional Low Dosage Regimens for Treatment of Moderate to Severe Acne

A further study was performed to establish that azithromycin dosage levels even lower than those of Examples 1 to 5 are efficacious in treating skin disorders. Five male subjects and five female subjects with moderate to severe facial acne vulgaris, having a mean age of 19.6 years, were treated either with 25 mg of oral azithromycin daily or with 80 mg of oral azithromycin every other day. Each of the ten subjects had acne nodules. The male subjects received the 25 mg per day regimen and the female subjects received the 80 mg every other day regimen. Treatment was continued for a duration of 6 weeks.

The numbers of facial inflammatory lesions: papules, pustules, and nodules, and non-inflammatory lesions: open and closed comedones, were counted at the beginning of treatment and again after 3 weeks of treatment and after 6 weeks of treatment. Additionally, nodules were counted independently at each of these visits. Additionally, during the treatment study, each subject reported the occurrence of any adverse effects. The results of this study for the 25 mg/day regimen are shown in Table 7 and for the 80 mg every other day regiment in Table 8. In these tables, the numbers represent the mean number of lesions in the four subjects of each group. The % decrease from Day 0 was calculated as the mean of the differences for each of the parameters (inflammatory lesions, non-inflammatory lesion and nodules) for each individual subject on Day 21 and Day 42.

TABLE 7

Azithromycin 25 mg/day for 6 weeks

| | Day 0 | Day 21 | % Decrease from Day 0 | Day 42 | % Decrease from Day 0 |
|---|---|---|---|---|---|
| Inflammatory lesions | 37.4 | 22.8 | 38.0% | 22.0 | 41.0% |
| Non-inflammatory lesions | 12.6 | 10.2 | 18.8% | 8.4 | 34.3% |
| Nodules | 3.0 | 1.6 | 45.0% | 1.2 | 58.3% |

TABLE 8

Azithromycin 80 mg every other day for 6 weeks

|  | Day 0 | Day 21 | % Decrease from Day 0 | Day 42 | % Decrease from Day 0 |
|---|---|---|---|---|---|
| Inflammatory lesions | 24.4 | 16.0 | 34.0% | 20.4 | 15.5% |
| Non-inflammatory lesions | 48.6 | 41.2 | 18.5% | 31.6 | 30.1% |
| Nodules | 3.8 | 1.0 | 76.0% | 1.8 | 58.0% |

The data in Table 7 establishes that dosages as low as 25 mg per day, when administered on a daily basis, are effective in treating skin disorders such as acne in adults. Similarly, the data in Table 8 establishes that low dose every other day therapy with each dose being as low as 80 mg is effective in treating such skin disorders.

During this study, only one adverse effect was reported in the subjects receiving 25 mg azithromycin per day and no adverse effects were reported in the subjects receiving 80 mg azithromycin every other day. The sole adverse effect reported was the occurrence of a migraine headache on day 21 in one subject. This adverse effect was deemed not to be related to the treatment. There were no typical antibiotic side effects reported, such as abdominal cramping, nausea, vomiting, diarrhea or vaginitis.

CONCLUSION

The studies establish that azithromycin, at dosages of less than 150 mg per day is effective in the treatment of acne, and especially the inflammatory lesions associated with acne. The low-dose azithromycin therapy was especially beneficial in the treatment of inflammatory acne nodules, an especially serious form of acne previously treated with isotretinoin. Because response to treatment with daily azithromycin was essentially the same whether the dosage was 120 mg, 80 mg, 40 mg, or 25 mg, or 80 mg every other day, it is conceived that daily treatment of acne with azithromycin at dosages even lower than 25 mg on a daily basis or 80 mg every other day are effective in reducing the signs and/or symptoms of acne and other skin conditions, and that the effectiveness of this treatment is not due to the antibiotic effect of azithromycin. Thus, it is conceived that daily doses of 5 to 25 mg, such as 10, 15, or 20, mg of azithromycin, or dosages of 10 to 75 mg administered on alternate days, are effective in treating the signs and/or symptoms of acne and other skin conditions.

It is also noted that, with daily administration of azithromycin in accordance with the invention, amelioration of acne signs and/or symptoms occurs very rapidly. Complete resolution of existing nodules in several subjects was noted at the examination at 21 days after initiation of treatment. Because lesions examined at 21 days following initiation of therapy were completely resolved at all dose levels tested in accordance with the method of the invention, it is clear that complete or partial resolution of such lesions necessarily had to have occurred earlier than by day 21. Therefore, it is conceived that resolution or improvement in the clinical signs and/or symptoms of acne occurs with the method of the invention in less than 3 weeks, such as within 1 week following commencement of therapy. Typically, drugs that have been approved by the FDA for treating acne have relied on data obtained over 10 to 12 weeks or more in order to be able to establish efficacy. The rapid resolution of acne lesions in patients with severe disease obtained by the method of the present invention, including inflammatory and non-inflammatory lesions, is unexpected and is not known to be obtained with presently available methods of treatment of acne, including present methods of treatment of acne with azithromycin.

Further, it is unexpected that azithromycin at any dose, and especially at the low doses in accordance with the method of the invention, would be effective in treating acne nodules, lesions associated with the more severe forms of inflammatory acne. Nodular acne heretofore has been treated with oral isotretinoin because of its severity and resistance to treatment. The only oral antibiotic specifically FDA-approved for acne treatment is minocycline tablets (Solodyne® tablets, Medicis Pharmaceutical Corporation, Scottsdale, Ariz.). However, the Solodyne package insert specifically disclaims use of the tablets for treatment of nodular acne. It is therefore particularly surprising that azithromycin, and especially azithromycin at the low doses described herein, would be so significantly and rapidly effective in reducing papules and pustules and resolving nodules in patients with such serious acne.

Accordingly, it is postulated by the present inventors that azithromycin may have both an antibiotic activity and an anti-inflammatory activity, and potentially other effects in addition to its antibiotic and anti-inflammatory effects. Unexpectedly, at levels that appear to be below that at which azithromycin has antibiotic activity, the present inventors have discovered that azithromycin retains its anti-inflammatory and other activity. Although wishing not to be bound by theory, it is this retention of anti-inflammatory and other activity at sub-antibiotic levels that is postulated to be at least one reason why low-dose azithromycin therapy in accordance with the present invention is effective in treating acne, and especially the inflammatory lesions of acne, and other skin diseases.

An important consideration pertaining to the present invention is that, over the course of therapy with azithromycin, the total amount of azithromycin administered is markedly reduced compared with prior art dosage regimens for azithromycin. The lowest published dosage of azithromycin of which the inventors are aware is that of Fernandez-Obregon, International Journal of Dermatology, 39:45-50 (2000), in which patients were administered 250 mg of azithromycin three times per week for an average of 11.67 weeks (Table 4, page 48). Thus, patients in this study received, on average, 8,752.5 mg of azithromycin. The lowest published total dosage of azithromycin known to the inventors for a six-week course of therapy is disclosed in Gruber, et al, Journal of Chemotherapy, 10(6):469-473 (1998), in which patients were administered 500 mg azithromycin daily for 4 days in four cycles every ten days, for a total of 8,000 mg. In contrast, patients treated with daily doses of 40 mg of azithromycin, or every other day doses of 80 mg of azithromycin, in accordance with the method of the invention for 12 weeks will receive only 3,360 mg of azithromycin, a reduction in total amount of azithromycin administered of about 4,500 to 5,500 mg, a reduction of about 62%. If treated for only 3 or 6 weeks with the low-dose regimen of the invention, a time period in which the low-dose regimen has been shown to be effective in the treatment of skin disorders such as severe acne, or treatment with doses of azithromycin less than 40 mg/day, an even greater reduction in total azithromycin administration will be obtained, as low as 560 mg to 1120 mg or lower total dose.

It has been discovered that prior art dosing regimens for azithromycin, particularly for treatment of skin diseases, and particularly for treatment of diseases that affect the pilosebaceous unit and especially sebum, is extremely wasteful of azithromycin and provides an unnecessary risk of unwanted side effects. It has been discovered that azithromycin levels in sebum, follicular casts, and skin reach a plateau at dosage levels of azithromycin well below those of the prior art. Thus, the waste of azithromycin and the side effects associated with prior art methods of administration are alleviated by the method of administration of the present invention.

It has been unexpectedly determined that daily, or every other day, treatment with low doses of azithromycin according to the method of the invention is effective in treating signs and/or symptoms of acne within 21 days, the earliest time tested, and is conceived therefore to be effective at times even earlier than this. Therefore, total dosages of azithromycin when treated with the low dose method of the invention may result in a nine-fold or greater decrease in total azithromycin administered, as treatment with the method of the invention has been found to be effective when total azithromycin administered is only about 10% or less of the dosage of the prior art (Gruber).

Because of the lower amounts of azithromycin administered compared with prior art dosage regimens, a significant advantage of the present invention is the reduction in potential adverse reactions due to long-term administration of azithromycin. As one example, medical treatment of acne typically persists for many weeks or even months, and in certain cases may persist for a period of years. Long-term therapy with low-dose azithromycin will dramatically reduce the incidence of serious adverse reactions that would otherwise occur due to therapy with higher doses of azithromycin that are presently prescribed. Such adverse reactions that may be reduced in incidence or severity include phospholipidosis, hepatic disorders, cardiovascular disorders such as tachycardia and hypotension, and pseudomembranous colitis. Other less serious but still common and troubling adverse events lead to poor patient compliance and discontinuance of therapy. Such adverse events include genitourinary disorders such as vaginal candidiasis and gastrointestinal distress including nausea and pain. It is envisioned that the method of the invention will reduce and minimize such problems due to the very small individual doses and total doses of azithromycin administered during a course of therapy. Furthermore, low dose azithromycin, in accordance with the invention, avoids and/or minimizes problems of resistance developing in pathogenic bacteria and other bacteria, including those implicated in skin diseases, such as *P. acnes* and *Staph. aureus* including MRSA.

While preferred embodiments of the invention have been described in detail, it will be apparent to those skilled in the art that the disclosed embodiments may be modified. It is intended that such modifications be encompassed in the following claims. Therefore, the foregoing description is to be considered to be exemplary rather than limiting, and the scope of the invention is that defined by the following claims.

The invention claimed is:

1. A pharmaceutical dosage form for oral administration comprising azithromycin in an amount less than 125 mg.

2. The pharmaceutical dosage form of claim 1 wherein the amount of azithromycin is 100 mg or less.

3. The pharmaceutical dosage form of claim 1 wherein the amount of azithromycin is 80 mg or less.

4. The pharmaceutical dosage form of claim 1 wherein the amount of azithromycin is 40 mg or less.

5. The pharmaceutical formulation of claim 1 that is a solid oral dosage form.

6. The pharmaceutical formulation of claim 5 that is in the form of a tablet or a capsule.

7. A kit for treating a skin disorder responsive to treatment with azithromycin comprising a container, a multiplicity of solid unit dosing forms of azithromycin within the container, wherein each solid dosing form within the container contains an amount of azithromycin of 125 mg or less, and instructions to administer one or more of the solid unit dosing forms containing a total amount of azithromycin of 125 mg or less at least three times per week.

8. The kit of claim 7 wherein the solid unit dosing forms are capsules or tablets.

9. The kit of claim 8 wherein the container contains a unit dose packaging.

10. The kit of claim 9 wherein the container is a blister pack.

11. The kit of claim 7 wherein the amount of azithromycin in each solid dosing form is 100 mg/day or less and the instructions are to administer one or more of the solid unit dosing forms containing a total amount of azithromycin of 100 mg or less at least three times per week.

12. The kit of claim 7 wherein the amount of azithromycin in each solid dosing form is 80 mg/day or less and the instructions are to administer one or more of the solid unit dosing forms containing a total amount of azithromycin of 80 mg or less at least three times per week.

13. The kit of claim 7 wherein the amount of azithromycin in each solid dosing form is 40 mg/day or less and the instructions are to administer one or more of the solid unit dosing forms containing a total amount of azithromycin of 40 mg or less at least three times per week.

14. A method for treating a skin disorder that is responsive to treatment with azithromycin in an individual suffering signs and/or symptoms therefrom comprising systemically administering azithromycin three or more days per week in an amount that is 125 mg of azithromycin or less per treatment day.

15. The method of claim 14 wherein the administration is for a duration of at least 20 days.

16. The method of claim 14 wherein the azithromycin is administered at an amount of 80 mg or less per treatment day.

17. The method of claim 16 wherein the azithromycin is administered at an amount of 40 mg or less per treatment day.

18. The method of claim 14 wherein the administration is at least every other day.

19. The method of claim 18 wherein the administration is at least 5 times per week.

20. The method of claim 19 wherein the administration is daily.

21. The method of claim 14 wherein the azithromycin is administered as a co-therapy with another medication that is effective in treating the skin disorder.

22. The method of claim 21 wherein the other medication is a topical retinoid and the skin disorder is acne.

23. The method of claim 14 wherein the skin disorder is acne.

* * * * *